United States Patent
Irwin et al.

(10) Patent No.: US 9,309,657 B2
(45) Date of Patent: Apr. 12, 2016

(54) FLOOR MAT

(71) Applicant: Impact Products, LLC, Toledo, OH (US)

(72) Inventors: John T. Irwin, Sylvania, OH (US); Stephen A. Dukes, North Baltimore, OH (US); Robert James Hayes, Westerville, OH (US); Donald James Staufenberg, Dublin, OH (US); Jeffrey C. Gayer, Sylvania, OH (US); Mark S. Woytowich, State College, PA (US); Brian Dennis Kratzer, Greer, SC (US); Dane R. Jackson, Port Matilda, PA (US)

(73) Assignees: Impact Products, LLC, Toledo, OH (US); New Pig Corporation, Tipton, PA (US)

( * ) Notice: Subject to any disclaimer, the term of this patent is extended or adjusted under 35 U.S.C. 154(b) by 187 days.

(21) Appl. No.: 13/826,005

(22) Filed: Mar. 14, 2013

(65) Prior Publication Data

US 2014/0076358 A1    Mar. 20, 2014

Related U.S. Application Data

(60) Provisional application No. 61/700,926, filed on Sep. 14, 2012.

(51) Int. Cl.
*E03C 1/264*    (2006.01)
*A47G 27/02*    (2006.01)
*A61L 9/12*    (2006.01)
*A61L 2/00*    (2006.01)
*E03D 13/00*    (2006.01)

(52) U.S. Cl.
CPC .......... *E03C 1/264* (2013.01); *A47G 27/0206* (2013.01); *A61L 2/00* (2013.01); *A61L 9/12* (2013.01); *E03D 13/005* (2013.01); *Y10T 428/23* (2015.01); *Y10T 428/237* (2015.01)

(58) Field of Classification Search
CPC .................................................. A47G 27/0206
USPC ......................................................... 428/192
See application file for complete search history.

(56) References Cited

U.S. PATENT DOCUMENTS

| 4,285,075 | A |   | 8/1981  | Nelson         |         |
|-----------|---|---|---------|----------------|---------|
| 4,459,710 | A |   | 7/1984  | Keyes et al.   |         |
| 4,480,341 | A |   | 11/1984 | Richards       |         |
| 4,480,342 | A |   | 11/1984 | Jones          |         |
| 4,530,118 | A |   | 7/1985  | Richards       |         |
| 4,609,580 | A |   | 9/1986  | Rockett et al. |         |
| 4,813,944 | A | * | 3/1989  | Haney et al.   | 604/358 |
| 5,784,746 | A |   | 7/1998  | Williams et al.|         |

(Continued)

*Primary Examiner* — David Sample
*Assistant Examiner* — Christopher Polley
(74) *Attorney, Agent, or Firm* — Fraser Clemens Martin & Miller LLC; James D. Miller

(57) ABSTRACT

A moppable floor mat is disclosed comprising a plurality of layers sharing a common peripheral boundary, the layers including an adhesive layer, a liquid impermeable layer, a high-traction layer, and a liquid absorbent layer. The adhesive layer is configured to be releasably adhered to a floor and capable of being mopped over without causing a movement of the moppable floor mat relative to a surface of the floor. The moppable floor mat further comprises a seal formed adjacent the peripheral boundary of the plurality of layers, wherein the seal is configured to form a fluid-tight barrier preventing liquids from exiting through the seal from the moppable floor mat.

17 Claims, 1 Drawing Sheet

(56) References Cited

U.S. PATENT DOCUMENTS

| | | |
|---|---|---|
| 6,055,679 A | 5/2000 | Goelz et al. |
| 6,295,658 B1 * | 10/2001 | Jenkins .............. A47G 27/0225 4/251.1 |
| 6,446,275 B1 | 9/2002 | Wright et al. |
| 7,093,773 B2 | 8/2006 | Kuiper |
| 2004/0253285 A1 | 12/2004 | O'Leary et al. |
| 2007/0110950 A1 * | 5/2007 | Yang .............................. 428/95 |
| 2008/0070025 A1 | 3/2008 | Pavlin |
| 2008/0092282 A1 | 4/2008 | Altmann et al. |
| 2008/0241091 A1 | 10/2008 | McGee et al. |
| 2009/0004234 A1 | 1/2009 | Kessler et al. |
| 2009/0053448 A1 * | 2/2009 | Paiva .................. A47G 27/0206 428/41.3 |
| 2009/0158512 A1 | 6/2009 | Stickler et al. |
| 2010/0030170 A1 * | 2/2010 | Keller et al. ................... 604/360 |
| 2010/0143645 A1 * | 6/2010 | Wilmsen ............ A47G 27/0206 428/116 |
| 2011/0318548 A1 | 12/2011 | Fedeli et al. |

* cited by examiner

FLOOR MAT

CROSS-REFERENCE TO RELATED APPLICATION

This application claims priority to U.S. Provisional Application Ser. No. 61/700,926, filed Sep. 14, 2012, the entire disclosure of which is hereby incorporated herein by reference.

FIELD OF THE INVENTION

The present disclosure relates to a moppable floor mat, and more specifically, to a floor mat having an adhesive underside surface and a liquid absorbent top surface capable of being mopped while still preventing slipping.

BACKGROUND OF THE INVENTION

There are many different applications for floor mats of various kinds. Floor mats are especially common in the bathrooms of non-residential buildings in the form of floor mats disposed under a hand dryer or urinal. Such floor mats are offered as non-slip surfaces to ensure that a user does not slip on any liquids that may have come in contact with the floor mat during use of a hand dryer or urinal.

One problem common to traditional bathroom floor mats is that the floor mats often fail to eliminate the undesirable odors associated with bathroom use. Floor mats for use with urinals and hand-dryers are especially susceptible to undesired odors as the floor mats are intended to shield the bathroom floor surface from such odorous liquids, especially urine. In some traditional floor mats, the urine or other odorous liquid is merely deposited on the floor mat, causing the odor coming from the floor mat to worsen significantly over time. Another problem associated with such floor mats is that a user who steps on the floor mat may unintentionally track any moisture or dirt found on the floor mat to another location exterior to the bathroom, causing additional odors and more areas in need of cleaning.

Traditional floor mats are also inconvenient in that they must be removed from the bathroom floor every time the bathroom floor is cleaned. Because bathroom floor mats often encounter bodily fluids and other contaminants, removal of such floor mats can be unsanitary and burdensome. Additionally, once the floor mat has been removed, it often must be cleaned separately, adding additional time and expense to the cleaning process. Alternatively, if a user does not remove the floor mat before cleaning, the bathroom floor must be cleaned around the floor mat, leaving the floor mat neglected as a potentially dirty, odor producing object.

Traditional floor mats also present a potentially dangerous surface for bathroom user to walk over. It is not uncommon for a bathroom user to trip or stumble over a floor mat, especially if a portion of the floor mat has folded over or gathered together. There is also a significant risk in the bathroom setting that a floor mat encountering various liquids will slip relative to both the bathroom floor surface and to a bathroom user's feet, causing further risk of injury to the user.

One solution to the issue of slippage has been the introduction of adhesive backed floor mats. However, many adhesive backed floor mats are problematic as they leave a residue behind that is difficult to clean or potentially damaging to the bathroom surface, often in the form of staining the grout that may be found between the tiles forming the bathroom floor surface. Many adhesive backed floor mats also present additional problems such as they are not easily removable from the bathroom floor surface, they are difficult to reposition once removed, and they use an adhesive that is not suitable for repeated reapplications to the bathroom floor surface.

One solution to these problems would be to create a bathroom floor mat that is capable of being cleaned along with the remainder of the bathroom in a manner that is sanitary and safe for a bathroom user. One method could be to create a floor mat that is capable of being mopped over with the remainder of the bathroom floor surface.

It is therefore desirable to have a floor mat that is capable of being mopped over, is effective at deodorizing the floor mat and surrounding area, is capable of being securely applied or reapplied to a floor surface without risk of moving relative to the floor surface, and that has a high-traction surface to prevent a user from slipping on the top surface of the floor mat.

SUMMARY OF THE INVENTION

Consonant with the present disclosure, a moppable floor mat that is releasably adhereable to a bathroom floor, minimizes odors, prevents slipping, and is capable of being mopped over with moving relative a bathroom floor surface, as well as a method of cleaning such a moppable floor mat, has surprisingly been discovered.

In one embodiment of the disclosure, a moppable floor mat comprises a plurality of layers sharing a common peripheral boundary, the layers including at least an adhesive layer and a liquid absorbent layer. The adhesive layer is configured to be releasably adhered to a floor and capable of being mopped over without causing a movement of the moppable floor mat relative to the floor. The moppable floor mat further comprises a seal formed adjacent the peripheral boundary of the plurality of layers, wherein the seal is configured to form a fluid-tight barrier preventing liquids from exiting through the seal from the moppable floor mat.

In another embodiment of the disclosure, a method of cleaning a moppable floor mat comprises: providing a floor mat comprising a plurality of layers sharing a common peripheral boundary and including at least an adhesive layer and a liquid absorbent layer, wherein the adhesive layer is configured to be releasably adhered to a floor and capable of being mopped over without causing a movement of the floor mat relative to the floor, and the moppable floor mat further comprises a seal formed adjacent the peripheral boundary of the plurality of layers, wherein the seal is configured to form a substantially fluid-tight barrier preventing liquids from exiting through the seal from the floor mat; locating the floor mat in a desired position on a surface of the floor with the adhesive layer in facing relationship with the surface of the floor; applying pressure to the floor mat in order to releasably adhere the adhesive layer to the surface of the floor; providing a mop at least partially saturated with at least one of water and a liquid cleaning solution; applying the mop to contact the floor mat; and moving the mop in a direction parallel to the surface of the floor while the mop is applied to the floor mat to remove any undesired materials from the floor mat.

DRAWINGS

The above, as well as other advantages of the present disclosure, will become readily apparent to those skilled in the art from the following detailed description, particularly when considered in the light of the drawings described hereafter.

DETAILED DESCRIPTION OF THE INVENTION

The following detailed description and appended drawings describe and illustrate various exemplary embodiments of the invention. The description and drawings serve to enable one skilled in the art to make and use the invention, and are not intended to limit the present disclosure, application, or uses.

Figure 1:
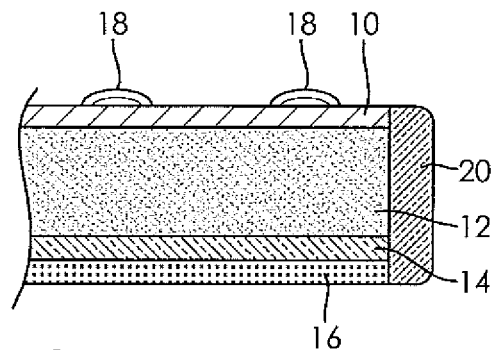
FIG. 1 shows a fragmented cross-sectional side view of a moppable floor mat according to an embodiment of the invention.
Figure 2:
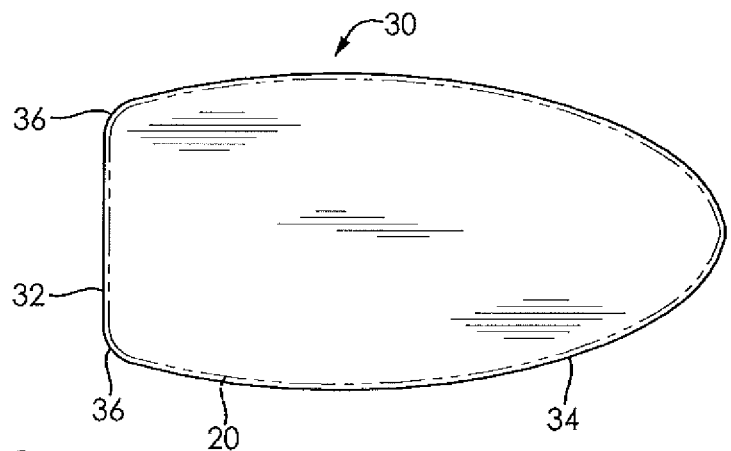
FIG. 2 shows a top plan view of the moppable floor mat depicted in FIG. 1 configured for use adjacent a urinal found in a bathroom.
Figure 3:
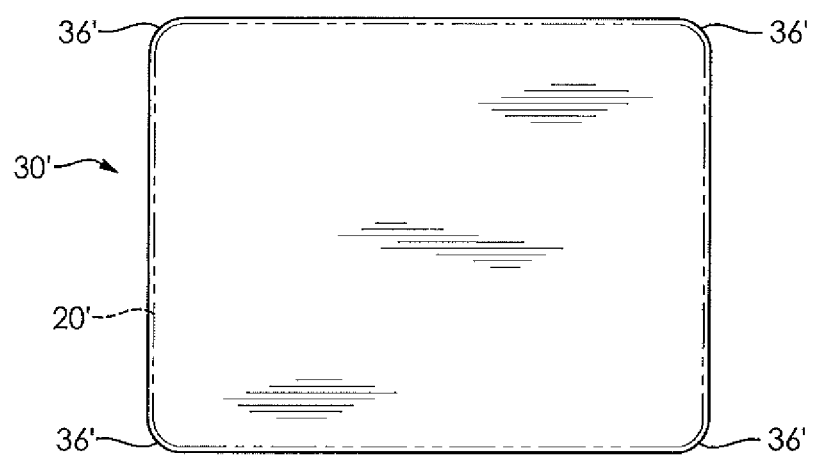
FIG. 3 shows a top plan view of the moppable floor mat depicted in FIG. 1 configured for use adjacent a hand-drying device found in a bathroom.

FIGS. 1-3 illustrate a moppable floor mat 30 according to one embodiment of the disclosure. The moppable floor mat 30 includes a plurality of layers 10, 12, 14, 16 and a sealed edge 20. The plurality of layers 10, 12, 14, 16 may be provided as an adhesive-backed absorbent mat material manufactured by the New Pig® Corporation located in Tipton, Pa. under the trade name of PIG® Grippy® Absorbent Mat, also described in United States Pat. Appl. Pub. No. 2011/0318548, hereby incorporated herein by reference in its entirety. The moppable floor mat 30 is used in a bathroom on a floor surface to militate against undesirable odors, slippage, and unnecessary cleaning procedures.

An arrangement of the plurality of parallel layers 10, 12, 14, 16 is illustrated in FIG. 1. Each of the layers 10, 12, 14, 16 is shaped and dimensioned to have a common boundary about a peripheral edge of the moppable floor mat 30. A high-traction layer 10 is disposed as an uppermost layer of the moppable floor mat 30 and is formed from a high-traction material. The high-traction layer 10 may be formed from a porous spunbond polymer. Materials that could be used to form the high-traction layer 10 include polypropylene, polyester, nylon, polyethylene, or any polymer having the properties necessary to be processed by a spunbonding procedure while remaining a high-traction material as desired, for example. The high-traction layer 10 offers many advantages over traditional floor mat surfaces. Because the high-traction layer 10 is formed from a spunbond material, it can be made to have high strength, high web integrity, and high-traction while still remaining porous. The porous aspect of the high-traction layer 10 allows any fluid that contacts the high-traction layer 10 to be quickly and easily transported to an adjacent liquid absorbent layer 12, allowing the high-traction layer 10 to remain a high-traction surface even when encountering a fluid.

The liquid absorbent layer 12 may be formed from a single layer or from multiple layers of a fine fiber polypropylene (FFP). The FFP is configured to absorb any number of liquids that may contact the moppable floor mat 30 including water, oils, grease, solvents, and urine. The FFP acts to quickly wick away liquids from the high-traction layer 10 shortly after contact, aiding the high-traction layer 10 in remaining a non-slip surface even when wet. The FFP is also configured to be capable of absorbing as much as 8 ounces of liquid for each square foot of the moppable floor mat 30. Even when at full capacity, the liquid absorbent layer 12 may dry completely in as little as 4 hours. The ability of the liquid absorbent layer 12 to wick away liquids from the top high-traction layer 10 while quickly evaporating the liquid allows the moppable floor mat 30 to greatly lessen any undesirable odors that may emanate from the liquid being absorbed.

The high-traction layer 10 and the liquid absorbent layer 12 may be attached to each other using a zig-zag, cross stitch, or other pattern of stitches 18. The stitches 18 pass through the high-traction layer 10 and the liquid absorbent layer 12 before looping back and extending out of the high-traction layer 10 for the process to be repeated. The addition of the stitches 18 aids in strengthening the layers 10, 12 while also adding an additional traction-forming feature adjacent the high-traction layer 10. The stitches 18 may be formed from any suitable polymer such as polyester.

Adjacent and beneath the liquid absorbent layer 12 is a liquid impermeable layer 14. The liquid impermeable layer 14 is configured to prevent any of the liquid that has been wicked to the liquid absorbent layer 12 from contacting either of an adhesive layer 16 disposed adjacent and beneath the liquid impermeable layer 14 and a bathroom floor surface. The liquid impermeable layer 14 may be formed from any light-weight material capable of preventing liquids traditionally encountered in a bathroom setting from passing through the material, including various forms of liquid impermeable polymers and the like.

The adhesive layer 16 is formed as a bottommost layer of the moppable floor mat 30. The adhesive layer 16 may be formed from a non-aggressive adhesive coated on a surface of the liquid impermeable layer 14. The adhesive is configured to prevent damage to traditional bathroom floor surfaces, to prevent permanent staining to various floor finishes or grout, and to not dissolve when encountering common bathroom liquids, including urine, water, and common mopping solutions. When the moppable floor mat 30 is adhered to a bathroom floor surface, the adhesive is configured to prevent movement of the moppable floor mat 30 in any direction running parallel to the bathroom floor surface. However, the adhesive is further configured to be releasably adhereable to the bathroom floor surface such that the moppable floor mat 30 can easily be peeled away from the bathroom floor surface if pulled in a direction perpendicular to the bathroom floor surface, allowing for easy removal and reapplication of the moppable floor mat 30, as desired. The adhesive layer 16 may include the properties described hereinabove and those described and disclosed in U.S. Pat. Appl. Pub. No. 2011/0318548.

As shown in FIGS. 1-3, the moppable floor mat 30 further includes a seal 20 formed adjacent a peripheral edge thereof. The seal 20 laminates the plurality of layers 10, 12, 14, 16 at the peripheral edge thereof while forming a substantially liquid-tight barrier, thereby preventing any liquids that have been absorbed by the water absorbent layer 12 from escaping the moppable floor mat 30. The seal 20 may be formed by a radio frequency welding procedure, but any appropriate method of securing the layers 10, 12, 14, 16 and forming a liquid-tight barrier may be utilized, including heat sealing, stitching, and bonding. The seal 20 is also beneficial in that it prevents the plurality of layers 10, 12, 14, 16 from peeling apart, curling, tearing, or delaminating. Although shown as rectangular and having a substantially linear or planar edge abutting the layers 10, 12, 14, 16, it is understood that the seal can have any shape as desired and any interface surface as desired with the layers 10, 12, 14, 16. The seal can also form a part of the layers 10, 12, 14, 16 or be a rigid or non-rigid frame joined to the layers 10, 12, 14, 16. The seal 20 may also include a hinged portion or other portion facilitating a pivoting of the floor mat 30 upwardly away from the floor to facilitate cleaning under the floor mat 30, if desired.

The various features described hereinabove allow the moppable floor mat 30 to easily be mopped if proper procedures are followed. First, a user should select an appropriate bathroom floor material, such as ceramic tiling, vinyl composite tile, porcelain, and marble. The user then cleans the bathroom floor surface to remove any contaminants that may affect the ability of the adhesive layer 16 to securely adhere to the bathroom floor surface. After cleaning the bathroom floor surface, the user should ensure that the bathroom floor surface is dry and devoid of any dust, sand, or soils. Next, the user locates the moppable floor mat 30 in a desired position with the adhesive layer 16 in facing relationship with the bathroom floor surface, making sure that the moppable floor mat 30 is pulled taught to eliminate any curls, folds, or peeled edges. The user then applies pressure to the moppable floor mat 30 along both the high-traction layer 10 and the seal 20, ensuring that the adhesive layer 16 is properly adhered to the bathroom floor surface. If the user wishes to reposition the moppable floor mat 30, the user grips the seal 20 and pulls in a direction perpendicular to the bathroom floor surface, peeling the moppable floor mat 30 away from the bathroom floor surface. The moppable floor mat 30 may then be reapplied to the bathroom floor surface as desired.

Once the moppable floor mat 30 has been adhesively secured to the bathroom floor surface in a desired position, it is capable of being mopped. The user applies a mop (not shown) at least partially saturated with at least one of water and liquid cleaning solution to the high-traction layer 10 and the seal 20, moving the mop over the moppable floor mat 30 repeatedly in any direction parallel to the bathroom floor surface while maintaining contact with the moppable floor mat 30. The mop removes any undesirable materials from the high-traction layer 10 that has not been wicked away to the liquid absorbent layer 12. Any water or cleaning solution deposited on the high-traction layer 10 will quickly be wicked away to the liquid absorbent layer 12, allowing the high-traction layer 10 to prevent slipping even when wet. The liquid absorbent layer 12 dries quickly even if completely saturated with a liquid. The liquid impermeable layer 14 prevents any liquid from the mopping procedure absorbed in the liquid absorbent layer 12 from contacting the adhesive layer 16, protecting the adhesive from any contamination. The seal 20 forms a barrier that prevents any liquid contained in the liquid absorbent layer 12 from leaving the moppable floor mat 30 in any direction parallel to the bathroom floor surface. The adhesive layer 16 prevents the moppable floor mat 30 from moving relative to the bathroom floor surface or peeling up during the mopping procedure. The features of the moppable floor mat 30 allow a user to clean the moppable floor mat 30 and the surrounding bathroom floor surface in one quick and easy cleaning procedure, greatly reducing time, labor, and expense.

The moppable floor mat 30 can take various shapes and forms. FIG. 2 shows a moppable floor mat 30 adapted for use adjacent a bathroom urinal. The moppable floor mat 30 has a shape along its peripheral boundary of a truncated elongate ellipse, including a straight edge 32 formed at a truncated longitudinal end of an elliptical edge 34. The transition from the straight edge 32 to the elliptical edge 34 may include chamfered corners 36, as shown in FIG. 2. The straight edge 32 is configured to allow a user to easily align the moppable floor mat 30 with a wall (not shown) from which the urinal extends. The user centers the straight edge 32 of the moppable floor mat 30 relative to the urinal and locates the straight edge 32 at least one of parallel to and flush with the wall adjacent the urinal. When in this position, the elliptical edge 34 is further configured to aid a user in aligning their feet adjacent the moppable floor mat 30. The elliptical edge 34 provides an ergonomic feature, allowing a user to position his feet on both short sides of the elongate elliptical edge 34 in a manner that is natural and comfortable to the user during use of the urinal.

In another embodiment of the device, a moppable floor mat 30' configured for use with a hand-drying device (not shown) such as a high-speed air-dryer or a towel-dispensing device is shown in FIG. 3. The moppable floor mat 30' has a shape of a rectangle or square having chamfered corners 36', but is otherwise identical to the elliptical moppable floor mat 30. The moppable floor mat 30' is installed by aligning one of four straight edges at least one of parallel to and flush with a wall (not shown) adjacent a hand-drying device. All other procedures for locating, cleaning, or removing the moppable floor mat 30' are the same as described hereinabove in reference to moppable floor mat 30. It should be understood that the moppable floor mat 30, 30' may be used for any purpose or be located anywhere in a bathroom depending on the application, as desired.

It should also be understood that the moppable floor mat 30, 30' may be used for any appropriate application outside of a bathroom. The moppable floor mat 30, 30' may be desirable for any application where a floor surface is commonly walked over and subjected to repeated contact with a liquid, regardless of the location of the floor surface. For example, such applications may include locating the moppable floor mat 30, 30' adjacent a drinking fountain or a dispenser of a hand sanitizes. The moppable floor mat 30, 30' provides a high-traction surface even if wet while also providing a surface capable of easy cleaning, odor reduction, and simple removal and reapplication, as desired.

EXAMPLE

Hereinafter, an example of a series of tests performed on the moppable floor mat 30, 30' is disclosed. The testing utilized both the truncated elliptical moppable floor mat 30 and the rectangular moppable floor mat 30'. Portable floors were built to demonstrate the effectiveness of the moppable floor mat 30, 30' on varying bathroom floor surface types (including ceramic tiling, vinyl composite tile, porcelain, and marble), grout patterns, and geometries in order to emulate the most common floor coverings found in typical consumer-facing business, industrial, and institutional restrooms. The damp mopping was performed using a standard side-press mop and bucket set-up. The testing took place in a climate controlled environment where the average temperature was approximately 67 degree Fahrenheit.

Testing was performed on all moppable floor mat 30, 30' samples located on the various flooring surfaces by mopping each sample once a day for a period of 30 days. Mopping was performed using a Ph neutral cleaning solution executed with a standard damp mopping procedure including moving the mop over each sample in a figure eight pattern in two different and perpendicular directions and then allowing each sample to air dry. The mop strands contacted the samples with normal and customary force and fashion to evaluate the moppable floormat 30, 30' on the basis of initial adhesion, intermediate adhesion, long term adhesion and removability, residue observed following removal, grout and tile staining, ability to be cleaned, and odor caused.

The initial adhesion test simulated a condition of initial floor preparation and adhesion of the test mat to several popular flooring types and grout patterns. The procedure included initial floor mopping followed by a glass cleaner application and towel drying procedure to ensure a clean and dry surface for initial application of the new moppable floor mats 30, 30'. Initial adhesion was acceptable on all samples on all floor types.

The intermediate adhesion test simulated a condition of intermediate adhesion of the test moppable floor mat 30, 30' to several popular flooring types and grout patterns pursuant to daily damp mopping in a figure eight pattern in two different and perpendicular directions, followed by an air drying procedure. Testing was performed up to day 15 whereby a walk-on test, a pivot test, and a finger peel test was executed to determine adhesion quality. Intermediate adhesion was very good on all samples and all floor types. It is important to note that adhesion actually improves with time, especially within the first 48 hours.

The long term adhesion and removal test simulated a condition of long term adhesion of the test moppable floor mats 30, 30' to several popular flooring types and grout patterns pursuant to daily damp mopping in a figure eight pattern in two different and perpendicular directions, followed by an air drying procedure. Testing was performed up to day 30 whereby a walk-on test, a pivot test, and a finger peel test was executed to determine adhesion quality. Removal after 30 days was executed manually with one hand. Testing for long term adhesion and removability showed all samples on all floor types to be of good to very good integrity. One sample, on day 27, was slightly peeled up by the mopping process, yet easily re-sealed. Upon investigation on day 30, the mat had maintained its seal and was in good order.

The odor and staining test simulated a condition of daily mopping and subjection of the test moppable floor mats 30, 30' to water over a 30 day period to determine their ability to seal out water and other contaminates from beneath the moppable floor mat 30, 30' itself. Additionally, odor, a byproduct of stagnant water trapped beneath the moppable floor mat 30, 30' and in the grout, was also tested. Daily damp mopping different and perpendicular directions with moderate downward force to remove foot traffic soils followed by an air drying procedure was performed up to day 30 whereby a staining test and odor test was executed to determine edge sealing integrity. Results of the odor test were negative. The staining test resulted in zero staining of the grout and tiles in all samples and all floor types even on mats that were flood mopped instead of damp mopped. This outcome demonstrates the ability of the moppable floor mat 30, 30' to seal off and protect the floor beneath it to ensure adhesion integrity, stain mitigation, and odor generation. Some residue was observed pursuant to removal of the moppable floor mats 30, 30' on day 30. Residue was minimal (2 mats with tactile discovery and slight visual identification) and easily cleaned.

The clean ability test simulated a condition of daily soiling of the test moppable floor mats 30, 30' which are mounted to several popular flooring types and grout patterns. Also tested was the ability of the moppable floor mat 30, 30' to remain affixed to the floor during top scrubbing. Testing included daily damp mopping different and perpendicular directions with moderate downward force to remove foot traffic soils followed by an air drying procedure. Testing was performed up to day 30 whereby a walk-on test, a pivot test, and a cleanliness test was executed to determine soil removal and adhesion quality. The moppable floor mats 30, 30' were also stepped upon to emulate foot traffic soiling. The moppable floor mats 30, 30' were then mopped in the prescribed fashion and demonstrated very good soil removal while maintaining adhesion integrity.

While certain representative embodiments and details have been shown for purposes of illustrating the invention, it will be apparent to those skilled in the art that various changes may be made without departing from the scope of the disclosure, which is further described in the following appended claims.

What is claimed is:

1. A moppable floor mat, comprising:
    a plurality of layers sharing a common peripheral boundary about an entirety of a periphery of each of the layers, the layers including at least an adhesive layer, a liquid absorbent layer, and a porous traction layer, wherein the adhesive layer is a pressure sensitive adhesive layer configured to be releasably adhered to a floor and capable of being mopped over without causing a movement of the adhesive layer relative to the floor, the traction layer configured to provide traction when wet by transporting liquid contacting the traction layer to the liquid absorbent layer through a plurality of pores formed in the traction layer, and the liquid absorbent layer configured to wick the liquid from the traction layer to the liquid absorbent layer; and
    a seal formed adjacent the peripheral boundary of the plurality of layers about the entirety of the periphery of each of the layers, wherein the seal is configured to form a substantially fluid-tight barrier preventing liquids from exiting through the seal from the liquid absorbent layer.

2. The moppable floor mat of claim 1, wherein the seal is formed by at least one of heat sealing, bonding, and stitching.

3. The moppable floor mat of claim 1, wherein the traction layer is a porous spunbond polymer configured to transport moisture to the liquid absorbent layer.

4. The moppable floor mat of claim 1, wherein the traction layer and the liquid absorbent layer are stitched together.

5. The moppable floor mat of claim 4, wherein the traction layer and the liquid absorbent layer are stitched together using a stitching material formed from polyester.

6. The moppable floor mat of claim 1, wherein the liquid absorbent layer is formed from a fibrous polypropylene.

7. The moppable floor mat of claim 1, further comprising a liquid impermeable layer, wherein the adhesive layer is disposed adjacent the liquid impermeable layer, the liquid impermeable layer is disposed adjacent the liquid absorbent layer, and the liquid absorbent layer is disposed adjacent the traction layer.

8. The moppable floor mat of claim 7, wherein the seal is formed by radio frequency welding each of the porous traction layer, the liquid absorbent layer, the liquid impermeable layer, and the adhesive layer together adjacent an entirety of the common peripheral boundary of the plurality of layers.

9. The moppable floor mat of claim 1, wherein the peripheral boundary of the plurality of layers has the shape of a truncated elongate ellipse including a substantially straight edge formed at a truncated longitudinal end of the body and an elongate elliptical edge.

10. The moppable floor mat of claim 9, wherein the straight edge is configured to align the floor mat flush with a wall adjacent a urinal and the elongate elliptical edge is configured to align feet of a user in a comfortable position adjacent the elongate elliptical edge during use of a urinal.

11. The moppable floor mat of claim 1, wherein the peripheral boundary of the plurality of layers has the shape of a rectangle having rounded corners.

12. A method of cleaning a moppable floor mat, comprising:
    providing a floor mat comprised of a plurality of layers sharing a common peripheral boundary about an entirety of a periphery of each of the layers, the plurality of layers including at least an adhesive layer, a liquid absorbent layer, and a traction layer, wherein the adhesive layer is a pressure sensitive adhesive layer configured to be releasably adhered to a floor and capable of being mopped over without causing a movement of the adhesive layer relative to the floor, the traction layer configured to provide traction when wet by transporting liquid contacting the traction layer to the liquid absorbent layer through a plurality of pores formed in the traction layer, and the liquid absorbent layer configured to wick the liquid from the traction layer to the liquid absorbent layer; the floor mat further including a seal formed adjacent the peripheral boundary of the plurality of layers, wherein the seal is configured to form a substantially fluid-tight barrier preventing liquids from exiting through the seal;

locating the floor mat in a desired position on a surface of the floor with the adhesive layer in facing relationship with the surface of the floor;

applying pressure to the floor mat in order to releasably adhere the adhesive layer to the surface of the floor;

providing a mop at least partially saturated with at least one of water and a liquid cleaning solution;

applying the mop to contact the floor mat; and moving the mop in a direction parallel to the surface of the floor while the mop is applied to the floor mat to remove any undesired materials from the floor mat.

13. The method of claim 12, further comprising the step of cleaning the surface of the floor prior to locating the floor mat to remove any undesired materials from the surface of the floor to ensure proper adhesion between the surface of the floor and the adhesive layer of the floor mat.

14. The method of claim 12, wherein the step of locating the floor mat further comprises aligning a straight peripheral edge of the floor mat parallel to a wall extending from the surface of the floor.

15. The method of claim 12, wherein prior to applying the mop to the floor mat the floor mat is removed from the surface of the floor and relocated to a desired position.

16. The method of claim 12, wherein the floor mat is removed from the floor by gripping the seal and pulling the floor mat in a direction perpendicular to the surface of the floor to peel the adhesive surface from the surface of the floor.

17. The method of claim 12, wherein prior to locating the floor mat a user pulls the floor mat to be taught to eliminate any curls, folds, or peeled edges formed thereon.

* * * * *